(12) United States Patent
Linden et al.

(10) Patent No.: US 11,026,608 B2
(45) Date of Patent: Jun. 8, 2021

(54) CEREBRAL OXIMETRY USING TIME-GATED DIRECT SEQUENCE SPREAD SPECTRUM

(71) Applicants: Kurt J. Linden, Wayland, MA (US); Laurence B. Milstein, La Jolla, CA (US)

(72) Inventors: Kurt J. Linden, Wayland, MA (US); Laurence B. Milstein, La Jolla, CA (US)

(73) Assignee: VOX BIOMEDICAL LLC, Bedford, MA (US)

( * ) Notice: Subject to any disclaimer, the term of this patent is extended or adjusted under 35 U.S.C. 154(b) by 507 days.

(21) Appl. No.: 15/864,177

(22) Filed: Jan. 8, 2018

(65) Prior Publication Data

US 2018/0192931 A1 Jul. 12, 2018

Related U.S. Application Data

(60) Provisional application No. 62/443,905, filed on Jan. 9, 2017.

(51) Int. Cl.
*A61B 5/1455* (2006.01)
*A61B 5/00* (2006.01)

(52) U.S. Cl.
CPC ...... *A61B 5/14553* (2013.01); *A61B 5/14552* (2013.01); *A61B 5/7203* (2013.01);
(Continued)

(58) Field of Classification Search
CPC .............. A61B 5/1455; A61B 5/14551; A61B 5/14552; A61B 5/14553; A61B 5/7225;
(Continued)

(56) References Cited

U.S. PATENT DOCUMENTS

| | | | | | |
|---|---|---|---|---|---|
| 5,822,363 | A | * | 10/1998 | Le Roy | H04B 1/707 375/143 |
| 2003/0109776 | A1 | * | 6/2003 | Jacques | A61B 5/1495 600/331 |
| 2006/0222224 | A1 | * | 10/2006 | Ohashi | A61B 5/14553 382/128 |

(Continued)

OTHER PUBLICATIONS

Gratton, E. et al., "Measurement of Brain Activity by Near-Infrared Light," Journal of Biomedical Optics, 10(1), Jan./Feb. 2005, pp. 011008-011013.

(Continued)

*Primary Examiner* — Chu Chuan Liu
(74) *Attorney, Agent, or Firm* — Hunter Clark PLLC

(57) ABSTRACT

A cerebral oximeter includes a first light source for emitting light in response to a first electrical signal, a second light source for emitting light in response to a second electrical signal, a first photodetector for detecting at least a portion of the light emitted from the first light source, and a second photodetector for detecting at least a portion of the light emitted from the second light source. The cerebral oximeter further includes a pseudonoise (PN) code modulator for modulating the first electrical signal and the second electrical signal using a spreading sequence to occupy an electrical bandwidth greater than necessary to send optical signal pulse amplitude information to a photodetector, and a time gate for filtering a first detection signal from the first photodetector and a second detection signal from the second photodetector based on a desired time-of-arrival.

20 Claims, 12 Drawing Sheets

(52) U.S. Cl.
CPC ............ *A61B 5/725* (2013.01); *A61B 5/7225* (2013.01); *A61B 5/7228* (2013.01); *A61B 5/7246* (2013.01); *A61B 5/7257* (2013.01); *A61B 2562/0238* (2013.01); *A61B 2562/043* (2013.01)

(58) Field of Classification Search
CPC ..... A61B 5/7246; A61B 5/7228; A61B 5/725; A61B 5/7203; A61B 5/7257; A61B 2562/043; A61B 2562/0238
See application file for complete search history.

(56) References Cited

U.S. PATENT DOCUMENTS

2008/0027299 A1*  1/2008  Tobola ............... A61B 5/02416
                                                    600/323
2017/0202465 A1*  7/2017  Bartling ............... A61B 5/7225

OTHER PUBLICATIONS

Kontos, A.P. et al., "Brain Activation During Neurocognitive Testing Using Functional Near-Infrared Spectroscopy in Patients Following Concussion Compared to Healthy Controls," Brain Imaging and Behavior, DOI 10.1007/s11682-014-9289-9.

Martelli, F. et al., "Light Propagation Through Biological Tissue and Other Diffusive Media, Theory, Solutions and Software," 2010, SPIE Press.

4. Boas, DA, et al., "Three-dimensional Monte Carlo Code for Photon Migration Through Complex Heterogeneous Media Including the Adult Human Head," 2002, Opt. Express 10(3), pp. 159-170.

5. Jacques, SL et al., "Optical Properties of Biological Tissues: a Review," 2013, Phys. Med. Biol. 58, pp. R37-R61.

7. Hinkley, D.V. (Dec. 1969). "On the Ratio of Two Correlated Normal Random Variables". Biometrika 56 (3):635-639. Doi: 10.2307/2334671. JSTOR 2334671.

* cited by examiner $$r_1(t) \rightarrow \otimes \rightarrow \boxed{\frac{1}{T}\int_0^T r_1(t)c_1(t)dt} = \hat{A}_1$$
$$\uparrow$$
$$c_1(t)$$

FIG. 6

CEREBRAL OXIMETRY USING TIME-GATED DIRECT SEQUENCE SPREAD SPECTRUM

CROSS-REFERENCE TO RELATED APPLICATIONS

This application claims the benefit of U.S. Provisional Application No. 62/443,905, filed Jan. 9, 2017, entitled "CEREBRAL OXIMETRY USING DIRECT SEQUENCE SPREAD SPECTRUM," the entire contents of which is hereby incorporated herein by reference.

BACKGROUND

A number of clinical evaluation techniques are available for identification of concussion and mild traumatic brain injury (mTBI) by means of brain imaging. Computerized tomography (CT), functional magnetic resonance imaging (fMRI), positron emission tomography (PET), electroencephalography (EEG) and magnetoencephalography (MEG) are among the most prominent of the technologies used for brain imaging studies. However, these modalities typically suffer from relatively low temporal resolution (CT, fMRI, PET) or spatial resolution (EEG, MEG). Computed tomography and positron emission tomography have the added drawback of employing ionizing radiation.

Recently, cerebral oximetry has been shown to be capable of identifying neurological brain health by its linkage to cerebral blood oxygenation (Gratton E, Toronov V, Wolf U, Wolf M, and Webb A. "Measurement of brain activity by near infrared light," 2005, J. Biomedical Optics 10(1), pp. 011008-1-13, incorporated by reference in its entirety), and more recently, it has been demonstrated to be capable of identifying concussions (Kontos A P, Huppert T J, Beluk N H, Elbin R J, Henry L C, French J, Dakan S M, and Collins M W, "Brain activation during neurocognitive testing using functional near-infrared spectroscopy in patients following concussion compared to healthy controls," Brain Imaging and Behavior 2014, DOI 10.1007/s11682-014-9289-9, incorporated by reference in its entirety). Cerebral oximeters are used to measure the oxygen saturation of blood in the patient's head and/or forehead. Oxygen saturation levels may be used to determine the degree of deviation from normality of brain neural response in patients subjected to, or suspected of being subjected to concussion, mild traumatic brain injury (mTBI) or other forms of brain trauma, or to patients suffering from dementia or numerous brain diseases such as MS, Alzheimer's disease, Parkinson's disease, ALS, depression, etc.

Generally, oximetry is a technique for monitoring the oxygen saturation of the blood of a person or an animal (referred to as a "patient"). The oxygen saturation of a patient's blood is a measurement of the percentage of available hemoglobin that is carrying oxygen. Thus, oxygen saturation can be determined by comparing the relative amount of oxygen carrying hemoglobin (referred to as "oxyhemoglobin") to the amount of hemoglobin that is not carrying oxygen (referred to as "deoxyhemoglobin"). Oximeters take advantage of the fact that oxyhemoglobin and deoxyhemoglobin have different light absorption spectra. Conventional cerebral oximeters consist of a red light source, a near infrared light source, and one or more photodetectors (PDs) typically located on the scalp a few cm from the point of light entry into the scalp. The PDs sense the amount of each wavelength type of light that is transmitted through, scattered but not absorbed by, and subsequently exits from the patient's brain tissue onto the PDs. This is referred to as the remitted light. The measured remitted light intensity values of the red and near infrared light can then be compared to one another to determine the amount of oxyhemoglobin relative to the amount of deoxyhemoglobin, which is the oxygen saturation of the patient's blood. This, in turn, provides information on the patient's relative state of neurological health when subjected to, for example, verbal and/or visual stimulation under controlled test conditions. Since concussion victims exhibit abnormal neurological brain function, cerebral oximetry can be used as a means of diagnosing concussion in a non-invasive and relatively inexpensive manner.

SUMMARY

An example of a cerebral oximeter includes a first light source configured to emit light within a first range of wavelengths in response to a first electrical signal and a second light source configured to emit light within a second range of wavelengths in response to a second electrical signal. The cerebral oximeter also includes a first photodetector configured to detect at least a portion of the light emitted from the first light source and subsequently scattered by tissue and a second photodetector configured to detect at least a portion of the light emitted from the second light source and subsequently scattered by tissue. It is also possible to arrange the cerebral oximeter such that a single PD may capture the light from different wavelength sources. The cerebral oximeter further includes two pseudonoise (PN) code modulators configured to modulate the first electrical signal and the second electrical signal using a spreading sequence to occupy an electrical bandwidth greater than necessary to send optical signal pulse amplitude information to a photodetector.

An example of a method of performing cerebral oximetry includes emitting light within a first range of wavelengths in response to a first electrical signal; emitting light within a second range of wavelengths in response to a second electrical signal; detecting at least a portion of the light emitted from the first light source and scattered by tissue; detecting at least a portion of the light emitted from the second light source and scattered by tissue; and modulating the first electrical signal and the second electrical signal using a spreading sequence to occupy an electrical bandwidth greater than necessary to send optical signal pulse amplitude information to a photodetector.

An example of a cerebral oximeter according to the disclosure includes a first light source configured to emit light within a first range of wavelengths in response to a first electrical signal, a second light source configured to emit light within a second range of wavelengths in response to a second electrical signal, a first photodetector configured to detect at least a portion of the light emitted from the first light source, a second photodetector configured to detect at least a portion of the light emitted from the second light source, a pseudonoise (PN) code modulator configured to modulate the first electrical signal and the second electrical signal using a spreading sequence to occupy an electrical bandwidth greater than necessary to send optical signal pulse amplitude information to a photodetector, and a time gate configured to filter a first detection signal from the first photodetector and a second detection signal from the second photodetector based on a desired time-of-arrival.

Implementations of such a cerebral oximeter may include one or more of the following features. The first photodetector and the second photodetector may have an electrical bandwidth sufficient to detect the pseudonoise (PN) code modulated spread spectrum light signals. The first photodetector and the second photodetector may be a single photodetector circuit. The first photodetector and the second photodetector may be configured to receive light signals from the first light source and the second light source in addition to thermal noise and external interference. The cerebral oximeter may include detection circuitry with sufficient electrical bandwidth so that an autocorrelation function of the spreading sequence has a main lobe that is narrower than a time separation of a desired signal and at least one multipath signal. At least one processor in the cerebral oximeter may be configured to measure characteristics of an optical channel traversed by the light emitted by the first light source or the light emitted by the second light source, and enhance an accuracy of a mathematical model used to model propagation of light from the first light source to the first photodetector. The at least one processor may be configured to generate a time-of-arrival spectrum, which grows more precise with increasing number of detected laser pulses. The cerebral oximeter may include a passive filter. The passive filter may be matched to the spreading sequence. The only input to the passive filter may be received from the first photodetector or the second photodetector.

BRIEF DESCRIPTION OF THE DRAWINGS

FIG. 6 is a schematic of the input to and output from a receiver.

DETAILED DESCRIPTION

Figure 1:
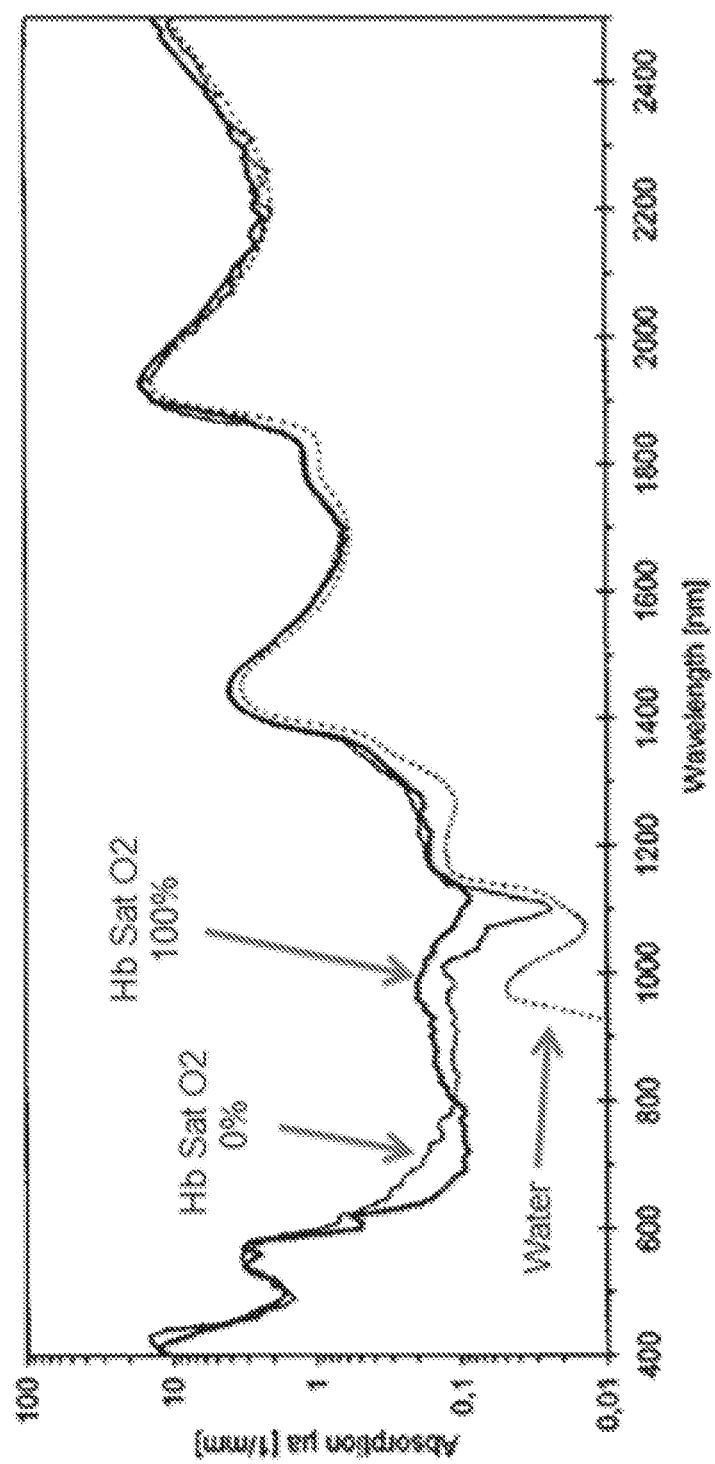
FIG. 1 is a graph of the absorption spectrum of oxyhemoglobin, deoxyhemoglobin and water for the wavelength range 400 nm-2500 nm.

At least the following four factors contribute to the feasibility of cerebral oximetry to assess the neurological state of brain health in a non-invasive manner: (a) human tissue is relatively transparent to red and near-infrared (NIR) light, particularly in the 600-1200 nm spectral region, (b) brain tissue is a turbid medium exhibiting strong forward light scattering, (c) the spectral absorption characteristics of oxygenated and deoxygenated blood differ from one another, and (d) neurological brain abnormalities such as mTBI have been shown to be associated with decreased cerebral blood oxygenation. Referring to FIG. 1, the difference in absorption spectra between oxyhemoglobin, deoxyhemoglobin and water is illustrated. Deoxyhemoglobin absorbs more light than oxyhemoglobin in the wavelength range from 600 nm to 800 nm and oxyhemoglobin absorbs more light than deoxyhemoglobin in the wavelength range from 800 nm to 1100 nm, with the absorption being equal at approximately 800 nm. For wavelengths greater than 1100 nm the absorption spectra of oxyhemoglobin and deoxyhemoglobin are nearly identical and are similar to the absorption spectrum of water.

The inventors have recognized and appreciated that conventional neurological testing is time consuming and expensive and that there is a need for fast, non-invasive measurement of neurological health for detecting brain injuries following concussion events. Such concussion events might occur among athletes, military battlefield personnel subject to explosive blasts or in general, individuals subjected to accidental head injury. In many cases involving head injury (concussion trauma) there is no outward appearance of brain injury since mTBI often has no outward appearing symptoms. A combination of factors such as head striking by an object, acceleration or deceleration movement of the brain not caused by direct physical contact with an object, or falls can result in TBI. An estimated 1.5 to 2 million people each year sustain brain injuries in the United States, mostly from accidents and sports.

The availability of compact narrow spectral width solid-state light emitters and sensitive high-speed PDs facilitate optical determination of cerebral blood oxygenation using a technique known as functional near-infrared spectroscopy (fNIRS). Decreased cerebral blood oxygenation, as measured using fNIRS correlates with mTBI making fNIRS-based cerebral oximetry a technique that may be used to diagnose brain trauma. However, current fNIRS instruments do not have the sensitivity or reliability for such diagnoses.

The inventors have appreciated and recognized that direct sequence spread spectrum (DSSS) technology may be used to improve optical signal detection as well as make it possible to identify the location of the source of a particular signal within the brain. In this way, ultra-high sensitivity cerebral oximetry may be performed at electronically selectable brain probe depths.

Examples of cerebral oximetry techniques involves the use of direct sequence spread spectrum (DSSS) technology in cerebral oximetry. Using DSSS and the associated detection circuitry may increase the sensitivity as well as allow identification of the location within the brain wherein a deviation from neuron response normality occurs. For example, cerebral oximetry using DSSS allows light scattered by the brain to be distinguished from unwanted light traversing different path lengths, such as through the scalp.

DSSS allows for precise measurement of the time of flight of light as it enters the brain near the light source and exits the brain near photodetectors placed at various locations on the scalp. This facilitates elimination of unwanted, shorter path leakage light that passes directly from the entry point of the light at the scalp to the photodetector on the scalp without traversing the brain tissue. Conventional cerebral oximeters attempt to reduce the impact of the scalp light leakage by subtracting the electrical signal output by a photodetector located near the point of light entry into the scalp from the electrical signal output from a photodetector located several centimeters away from the point of light entry. Such electrical signal subtraction, however, typically does not eliminate the detrimental effects of the light leakage.

Figure 2:
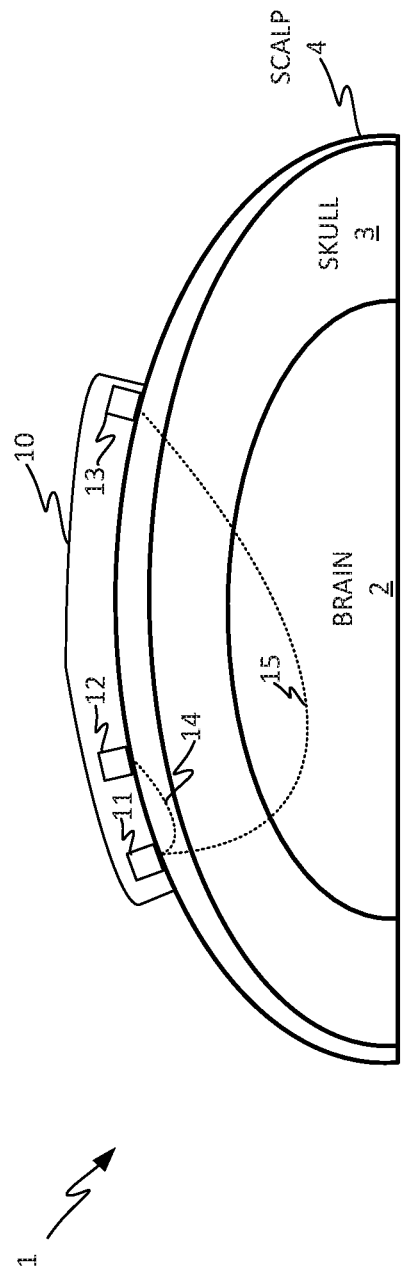
FIG. 2 is an example cerebral oximeter optode placed on a patient's head.

Referring to FIG. 2, a patient's head 1 is fitted with a cerebral oximeter optode 10. In a simplified model, the patient's head 1 includes a brain 2, a skull 3 and a scalp 4. The cerebral oximeter optode 10 is non-invasive and rests on the skin of the scalp 4. The cerebral oximeter optode 10 includes one or more light sources and/or one or more PDs. For example, cerebral oximeter optode 10, as illustrated in FIG. 2, includes a light source 11, a scalp PD 12 and a brain PD 13. Light may travel from the light source 11 to the scalp PD 12 and the brain PD 13 via various light paths. For the sake of clarity, a single, simplified light path 14 illustrates the light propagating from the light source 11 to the scalp PD 12 through the scalp 4, and a single, simplified light path 15 illustrates the light propagating from the light source 11 to the brain PD 13 through the scalp 4, skull 3 and brain 2. Sub-skin light paths, involving light transmission not only over and along the skin surface but also via underlying adipose layers, have a significant effect on the oximeter readings. Reduction of the effect of alternative light paths that do not propagate through the brain 2 increases the sensitivity of cerebral oximeter. As discussed below, time gated DSSS technology can be used to distinguish the desired light path from alternative, undesirable light paths.

A cerebral oximeter whose optode contains a light source 11 that uses DSSS to modulate the emitted light is capable of rejecting signals resulting from light paths other than the light path that propagates the region of the brain 2 being probed by the cerebral oximeter by means of time gating. The cerebral oximeter uses DSSS to impose a coded modulation on a light source with a particular temporal pulse width emitted by light source 11 such that the light pulse occupies an electrical bandwidth greater than necessary to transmit a pulse of light of that particular temporal pulse width. The electrical bandwidth is spread using a code that is independent of the received PD light signal. The independence of the code distinguishes DSSS modulation from standard modulation schemes in which the data modulation produces a spread of the light pulse spectrum. In DSSS, a signal receiver (e.g., scalp PD 12 and brain PD 13) synchronizes to the code to recover the received PD light signal. The use of DSSS in transmitting and receiving the electrically modulated optical signal allows for the separation of photodiode detector signals originating from different optical channel lengths by means of time gating. If the time associated with the different light path lengths is longer than the system response time the system will be able to distinguish between the different light path length signals. The system response time is related to the reciprocal of the system electrical bandwidth. Since current commercially available silicon PDs have ~30 GHz electrical bandwidths, the DSSS signal detection system will be able to distinguish between optical light path lengths of the order of a cm or possibly less. Since the typical penetration depth of red and IR light into the brain is of the order of a few cm, the time gated DSSS technology is applicable with the simultaneous ability to electronically select light path length through the brain, thereby making it possible to pinpoint the brain location that is being measured.

The dynamics of light propagation in the brain and its surrounding tissue is important to understanding DSSS-based data acquisition methodology in cerebral oximetry. Over the past two decades the results of diffuse optical tomography, dealing with the propagation of light in the brain, have been compared with other brain imaging methods such as MRI, CT, X-ray and ultrasound. These results have led to the development of mathematical models dealing with 3-D light propagation in the human brain. Such mathematical models provide information on spatial and temporal photon flux penetration into the human brain as well as remitted photon flux from the brain towards the surface of the head where it can be detected with high-speed PDs (Martelli F, Del Bianco S, Ismaelli A, and Zaccanti G. *Light propagation through biological tissue and other diffusive media.* 2010, SPIE Press, incorporated by reference in its entirety).

Figure 3B:
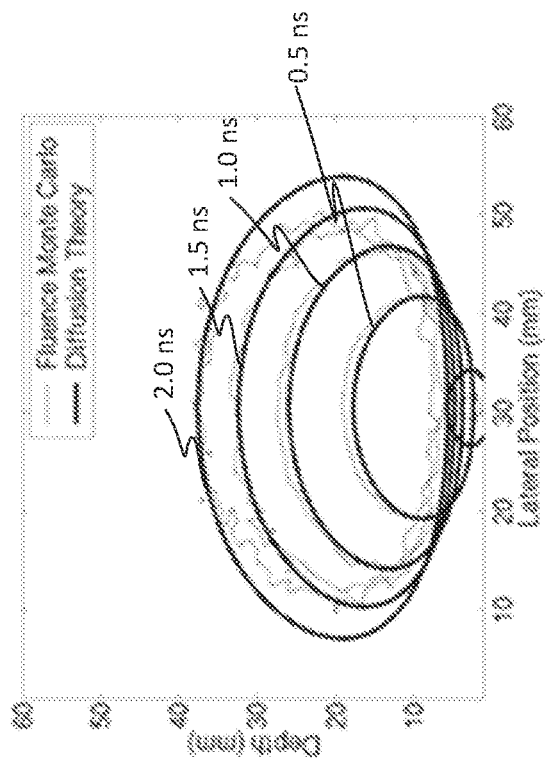
FIG. 3B is a plot of the temporal response to a light pulse showing iso-contours within the medium at 0.1 ns (innermost), 0.5 ns, 1.0 ns, 1.5 ns, and 2.0 ns (outermost).
Figure 3A:
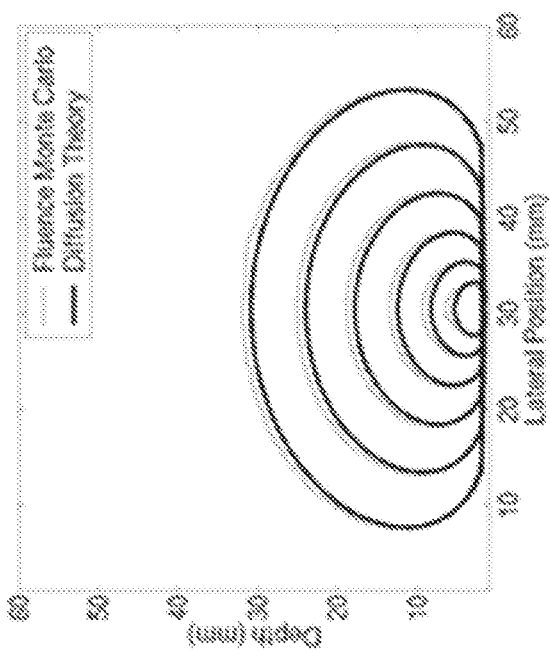
FIG. 3A is a plot of photon fluence within a semi-infinite, uniform tissue medium for an index-matched surface at zero depth with contours corresponding to 10 dB fluence separations, strongest near 30 mm
Figure 4B:
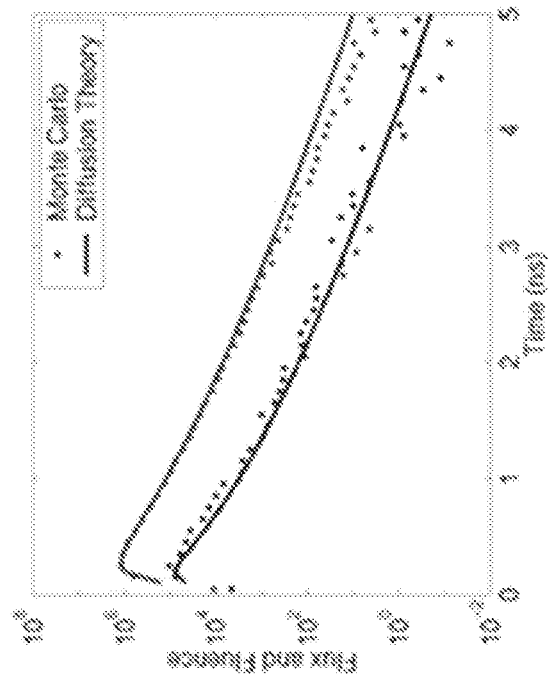
FIG. 4B is a plot of the temporal response of the remitted light pulse as measured at a depth of 10 mm below the scalp surface, 15 mm from the light source (top line) and the same remitted light fluence but at the scalp surface, 15 mm from the light source (bottom line). These calculated plots assume a semi-infinite brain medium.
Figure 4A:
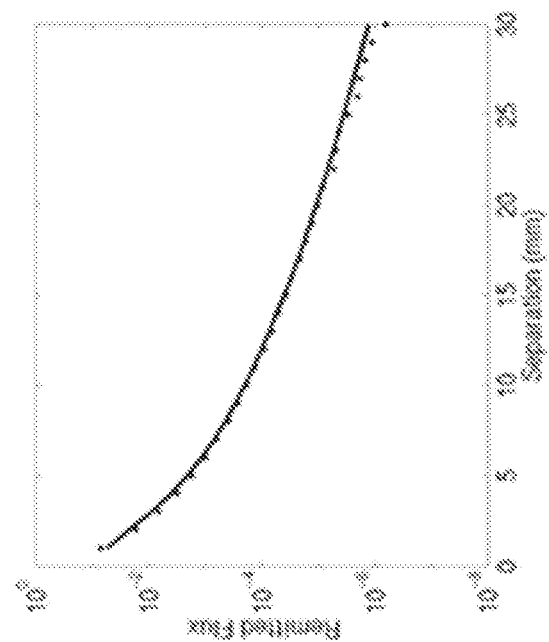
FIG. 4A is a plot of remitted photon flux on the surface of a semi-infinite medium as a function of distance between the light launch site and the remitted photon flux measurement site.

A mathematical model based on the dynamics of light propagation in a homogeneous, semi-infinite, simplified tissue medium where the light source consists of a collimated beam of light entering the medium as a point source at normal incidence has been described and evaluated (see Boas D A, Culver J P, Stott J J and Dunn A K. "Three-dimensional Monte Carlo code for photon migration through complex heterogeneous media including the adult human head," 2002, Opt. Express 10(3), pp. 159-170, incorporated herein by reference in its entirety). Based on the model assumptions, calculations were carried out using a realistic light scattering coefficient of 1 $mm^{-1}$, a scattering anisotropy, g=0.01 (where g is defined as the average cosine of the scattering angle and is a measure of the highly forward directionality of the elastic light scattering), and an optical absorption coefficient of 0.005 $mm^{-1}$, all of which have been shown to be realistic values for red and NIR light scattering by turbid tissue (See Jacques S L. "Optical properties of biological tissues: a review," 2013, Phys. Med. Biol. 58, pp. R37-R61, incorporated herein by reference in its entirety). Boas, et. al., calculated values of photon fluence within a semi-infinite tissue medium of uniform composition are shown in FIG. 3A. Here the plotted contours correspond to 10 dB fluence separations. From this plot it can be seen that the photon fluence decreases by approximately 50 dB at a depth of 30 mm into the tissue. Correspondingly, in the time domain, the light pulse corresponding to the 30 mm depth into the tissue is delayed by times ranging from hundreds of ps to several ns, as indicated in FIG. 3B. In Boas, et. al., the relative intensity of the remitted light observed on the surface of the tissue as a function of distance between the light launch site and the remitted light measurement site is illustrated in FIG. 4A. In FIG. 4A, it is shown that the calculated remitted light flux diminishes from the launch light flux intensity by a factor of approximately −50 dB at a 20 mm distance between the launch site and the measurement site. FIG. 4B illustrates the temporal decrease in remitted (i.e., abated as a result of photon absorption and scattering) light fluence at a depth of 10 mm below the scalp surface, 15 mm from the light source (upper line is from diffusion theory and upper points are from Monte Carlo calculations), and the same remitted light fluence at the surface of the scalp, 15 mm from the light source (lower line is from diffusion theory and lower points are from Monte Carlo calculations.) The latter (lower line) temporal light intensity is approximately two orders of magnitude weaker. According to Boas, et. al., it is assumed that after 10 ns the probability of photon detection in tissue is exceedingly small.

The mathematical model and representative tissue light propagation parameter of Boas, et. al. illustrated in FIGS. 3A-B and FIGS. 4A-B provide useful and important information about light propagation in the brain that can be used in a time gated DSSS-based cerebral oximeter. An advantage of using DSSS is its ability to allow the simultaneous reception of different wavelength signals in the presence of both thermal noise and external interference. However, for DSSS to provide these advantages, the bandwidth of the light signals used are sufficiently broad such that the autocorrelation function of the spreading sequence has a main lobe that is narrower than the time separation of each desired signal and its corresponding multipath. As visualized in the time domain, since brain tissue has an effective refractive index of ~1.5, the time for unscattered light to travel a distance of 2 cm in the brain is approximately 0.1 ns (100 ps). Consequently, to achieve a spatial resolution of 2 cm or less, the response time of the PD should be ~100 ps (corresponding to an electrical bandwidth of 10 GHz.) Further, the degree of interference suppression capability of the DSSS technique should be sufficiently large so as to attenuate both the external interference and the multiple access interference so that the net interference does not result in poor estimates of the amplitudes that are being measured. The bandwidth of the channel may be determined based on the relative strengths of the different optical wavelength signals, and is expected to have a value of the order of 10 GHz.

Two different light emitters of different wavelengths may be used, typically one wavelength below 800 nm and one wavelength above 800 nm. Further, any characteristics of the light-traversal channel (either statistical or deterministic) that can be provided will enhance the accuracy of the mathematical model and hence enhance the usefulness of the final results. The quantitative examples of light attenuation into a semi-infinite brain tissue medium shown in FIGS. 3A, 3B, and FIGS. 4A and 4B, based on a realistic mathematical model, illustrate expected light propagation characteristics in the brain. Light propagation through skull and thin, multi-layer scalp tissue could be somewhat different, but of a similar order of magnitude and with a shorter distance of travel through layers that are much thinner than the bulk brain tissue material. Significantly, FIG. 3B illustrates that the measured time-of-flight for photons to traverse an effective distance corresponding to a brain tissue depth of 2 cm beneath the scalp is of the order of 1 ns, which is approximately a factor of 10 longer than the 0.1 ns duration for light travel under unscattered conditions, as noted above. Thus, the effect of the strong brain tissue light scattering is to effectively lengthen the time of remitted photon flight in brain tissue by a factor of approximately 10 above that expected if the photons were not strongly scattered. This suggests that the electrical signal bandwidth of both the laser light source and PD may be reduced from 10 GHz to approximately 1 GHz, greatly reducing system complexity and cost.

Figure 5:
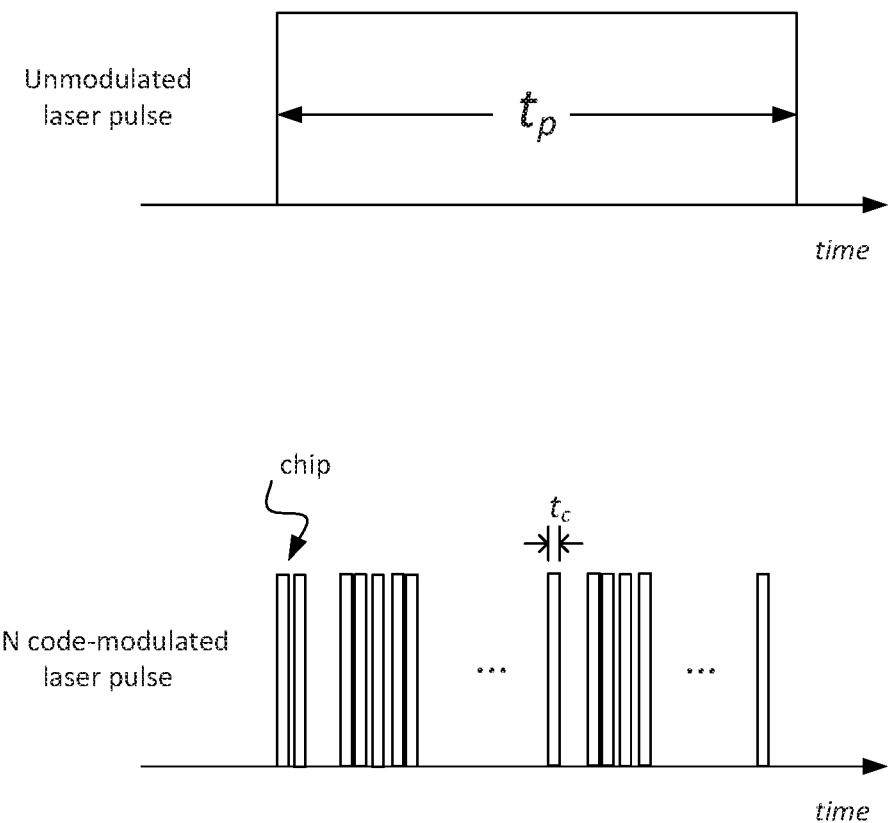
FIG. 5 is a plot of an unmodulated laser pulse and a pseudo-noise-code modulated laser pulse.

Referring to FIG. 5, a PN chip sequence with a chip duration $t_c$ is compared to an unmodulated light pulse of duration $t_p$. The top portion of this figure shows the laser pulse length while the bottom portion of this figure shows the PN chip sequence that occurs during the laser pulse.

Once the channel bandwidth and channel attenuation are available the DSSS oximetry technique can be performed. The DSSS oximetry technique may include determining the values for parameters, such as chip rate, spreading sequence period, and processing gain. These parameters are determined using the available bandwidth (which must be at least 1 GHz, but preferably 10 GHz), the required information rate (which can vary and be determined by practical application considerations), the allowable complexity of the receiver (determined by final product pricing goals), and time constraints on how quickly the received waveforms need to be processed (determined by equipment operational requirements). It may also include receiver design, with perhaps the most serious challenges being the mechanism to detect the two desired signal components in the presence of multiple attenuated and delayed versions of those signals, and to initially synchronize the locally-generated spreading sequences to the spreading sequences of the received waveform. However, code synchronization of pseudorandom noise code (PN-code) may not be necessary in oximetry applications because "time zero" is determined by the start of the laser pulse.

The front end of the receiver consists of one or more PDs which receive the photons remitted from the brain and provide a voltage (or current) output signal whose amplitude is proportional to the intensity of the incident light flux (number of photons per second). The PDs must be fast enough to respond to the short (~100 ps) received light pulses. Commercially available MSM PDs have rise and fall times of the order of 30 ps (Hamamatsu GaAs MSM PD, series G-4176) and are fast enough to respond to 100 ps light pulses in the 700-850 nm spectral region. The PD signals must then be amplified by amplifiers with an electrical bandwidth of the order of 10 GHz and then fed into the A/D converter preceding the matched filter described below. Light source bandwidths of the order of 10 GHz (100 ps rise times) are available in the form of vertical cavity surface emitting lasers (VCSELs) from Vixar, Inc. or other laser diodes such as those produced by Jenoptik. Modules designed for diffuse optical spectroscopy as required for cerebral oximetry instrumentation, consisting of three VCSEL chips contained in one transistor-type package emitting at 680 nm, 795 nm, and 850 nm are commercially available at reasonable prices.

As an example, cerebral oximetry using DSSS uses at least two transmitted optical signals, given by:

$$s_1(t)=A_1c_1(t) \text{ and } s_2(t)=A_2c_2(t), \quad \text{Eqn. (1)}$$

where $A_i$ and $c_i(t)$ are the laser pulse amplitude and spreading sequence, respectively, of signal i, i=1, 2. At the input to receiver 1, as shown schematically in FIG. 6, the waveform is given by $$r_1(t)=s_1(t)+\Sigma_{j=1}^J \infty_{1j} s_1(t-T_{1j})+\infty s_2(t-T)+\Sigma_{j=1}^J \infty_{2j} s_2(t-T_{2j})+n_w(t) \quad \text{Eqn. (2)}$$

where J is the number of multipath components due to either $s_1(t)$ or $s_2(t)$, T is the delay (relative to $s_1(t)$) and α is the attenuation of $s_2(t)$ at the input to receiver 1, and the $\{\infty_{1j}\}$, $\{\hbar_{2j}\}$, $\{T_{1j}\}$ and $\{T_{2j}\}$ represent the attenuations and time delays, respectively, of the various multipath components, which can be very large. Lastly, $n_w(t)$ represents the addition of a white Gaussian noise (AWGN).

The interference that the presence of $s_2(t)$ imposes upon $s_1(t)$ is referred to as I(t), which is given by $$I(t)=\infty A_2 c_2(t-c)+\Sigma_{j=1}^J \infty_{2j} A_2 c_2(t-T_{2j}) \quad \text{Eqn. (3)}$$

The estimate of $A_1$, denoted by $\hat{A}_1$, is given by $$\hat{A}_1 = A_1 + A_1 \sum_{j=1}^{J} \alpha_{1j} \frac{1}{T} \int_0^T c_1(t) c_1(t - \tau_{1j}) dt + \alpha \qquad \text{Eqn. (4)}$$

$$A_2 \frac{1}{T} \int_0^T c_1(t) c_2(t - \tau) dt +$$

$$A_2 \sum_{j=1}^{J} \alpha_{2j} \frac{1}{T} \int_0^T c_1(t) c_2(t - \tau_{2j}) dt + N(T)$$

$$= A_1 + A_1 \sum_{j=1}^{J} \alpha_{1j} R_{c_1}(\tau_{1j}) + \alpha \qquad \text{Eqn. (5)}$$

$$A_2 K_{c_1 c_2}(\tau) + A_2 \sum_{j=1}^{J} \alpha_{2j} K_{c_1 c_2}(\tau_{2j}) + N(T),$$

where $R_c(x)$ is the autocorrelation function of $c_1(t)$, $k_{c_1,c_2}(x)$ is the cross-correlation between $c_1(t)$ and $c_2(t)$, and $N(T)$ is due to the AWGN.

One mode of cerebral oximeter operation that is of particular interest when changes in neurological brain function are to be measured, as for example in victims of concussion or traumatic brain injury (TBI), is to measure human brain response to visual or verbal stimuli. In such brain function measurements, it is not the absolute value of cerebral blood oxygen saturation that is of importance, but rather, the degree of cerebral blood oxygenation change as a consequence of neurological brain function change. For example, a concussion victim's relative cerebral blood oxygenation level can be measured while the victim is subjected to visual or verbal stimuli. Prior experiments have demonstrated that there are differences in neurologically evoked brain blood oxygenation levels between normal subjects and victims of concussion (Kontos A P, Huppert T J, Beluk N H, Elbin R J, Henry L C, French J, Dakan S M, and Collins M W, "Brain activation during neurocognitive testing using functional near-infrared spectroscopy in patients following concussion compared to healthy controls," Brain Imaging and Behavior 2014, DOI 10.1007/s11682-014-9289-9, incorporated by reference in its entirety). Thus, measurement of the relative values of $A_1$ and $A_2$ provide indirect but meaningful information on the relative neurological state of brain health. A variety of algorithms can be used to measure changes in the relative values of parameters $A_1$ and $A_2$, for example $A_1/A_2$. In this case, the parameter of interest is $$z \triangleq \frac{\hat{A}_1}{\hat{A}_2} \qquad \text{Eqn. (6)}$$

and the pdf of z is given by the following integral:

$$f_Z(z) = \int_{-\infty}^{\infty} |\hat{a}_1| f_{\hat{A}_1,\hat{A}_2}(z\hat{a}_2,\hat{a}_2) d\hat{a}_2 \qquad \text{Eqn. (7)}$$

In Eqn. (7), $f_{\hat{A}_1,\hat{A}_2}(\hat{a}_2, \hat{a}_2)$ is the joint pdf of $\hat{A}_1$ and $\hat{A}_2$. Because of the complex nature of $\hat{A}_1$ and $\hat{A}_2$, it is doubtful that a tractable analytic expression for $f_Z(z)$ can be found. However, if J (the number of multipath components as discussed above) is sufficiently large, a central limit theorem might be applicable so that $\hat{A}_1$ and $\hat{A}_2$ can be approximated as being jointly Gaussian. For this case, if $\hat{A}_1$ and $\hat{A}_2$ can be shown to be independent, then an expression for the pdf of z can be found in (Hinkley, D. V. (December 1969). "On the Ratio of Two Correlated Normal Random Variables". Biometrika 56 (3): 635-639. Doi: 10.2307/2334671. JSTOR 2334671.), and is given below. For simplicity of notation, we replace $\hat{A}_1$ by X and $\hat{A}_2$ by Y. Assuming X is Gaussian with mean $\mu_x$ and variance $\sigma_x^2$, with similar notation for Y, and assuming that X and Y are independent, then, with $$Z = \frac{X}{Y},$$

we have $$f_z(z) = \frac{b(z) \cdot d(z)}{a^3(z)} \frac{1}{\sqrt{2\pi\sigma_x\sigma_y}} \left[ \Phi\left(\frac{b(z)}{a(z)}\right) - \Phi\left(\frac{b(z)}{a(z)}\right) \right] + \frac{1}{a^2(z) \cdot \pi\sigma_x\sigma_y} e^{-\frac{c}{2}}$$

where $a(z) = \sqrt{\frac{1}{\sigma_x^2} z^2 + \frac{1}{\sigma_y^2}}$ $b(z) = \frac{\mu_x}{\sigma_x^2} z + \frac{\mu_y}{\sigma_y^2}$ $c = \frac{\mu_x}{\sigma_x^2} + \frac{\mu_y}{\sigma_y^2}$ $d(z) = e^{\frac{b^2(z) - ca^2(z)}{2a^2(z)}}$ and $\Phi$ is the cumulative distribution function of the normal distribution $$\Phi(t) = \int_{-\infty}^{t} \frac{1}{\sqrt{2\pi}} e^{-\frac{1}{2} u^2} du.$$

An approach to test whether or not the central limit theorem holds may include, for example, a test, via computer simulation, how close to Gaussian the two estimates are.

Other tests may include the analysis and solution of these equations under various assumed conditions utilizing previously published parameters for the velocity of light in the brain medium as illustrated in FIGS. 3A-B and FIGS. 4A-B. One or more models may be presented for a variety of time delays for realistic light paths involving the desired cortex light path, alternative cortex light paths, skin and underlying adipose tissue light paths, surface leakage light paths and motion artifact light paths. In some examples, there may be some overlap between the desired sub-cortex light path and some of the possible alternative light paths of equal optical length, but the effect of the optical signal from such light paths may be less than in conventional (non-DSSS) cerebral oximeters.

Cerebral oximetry using DSSS uses a DSSS signal and a correlator or matched filter for separating and eliminating unwanted multipath signals. The paths which traverse through the brain are the paths that are of interest for cerebral oximetry; the paths that traverse the exterior of the skull is a source of interference. Additionally, if a path that traverses the exterior of the skull is mistakenly taken to be the desired signal, it would produce meaningless results.

Thus, to ensure the signal of interest is the signal being measured, the cerebral oximeter can use either a conventional DSSS receiver correlator structure, or a time invariant matched filter that automatically convolves the received waveform with the filter's impulse response. The distinction between a correlator and a matched filter is that the former is an active device (i.e., it has two inputs, namely the received signal and a locally-generated replica of the spreading sequence of the signal-of-interest) operating in the time domain, whereas the latter is a passive device, in that it is a time-invariant linear filter whose only input is the received waveform. A correlator would be required to perform a serial search of all unknown phase positions of the spreading sequence in order to properly synchronize itself to the phase of the received waveform. On the other hand, a matched filter, being a passive device, automatically convolves the received waveform with the filter's impulse response.

The matched-filter based receiver is able to receive the sequence of waveforms consisting of the signals that entered the brain and all the multipath signals that traversed paths which did not enter the brain. As each waveform passed through the matched filter, a narrow pulse with a large amplitude would be seen at the output (this is due to the de-spreading operation of a DSSS signal). These pulses would be continuously separated in time due to the continuous difference in path length of the various paths traversed by the remitted signals. If the difference in arrival times of adjacent reflections was greater than or equal to the chip duration of the spreading sequence, these paths could be individually identified. Lastly, if the receiver has some prior knowledge of the expected ordering (in time of arrival) of these paths, it would be possible to isolate the ones that penetrated the brain to a desired depth, and ignore all the others.

Figure 7:
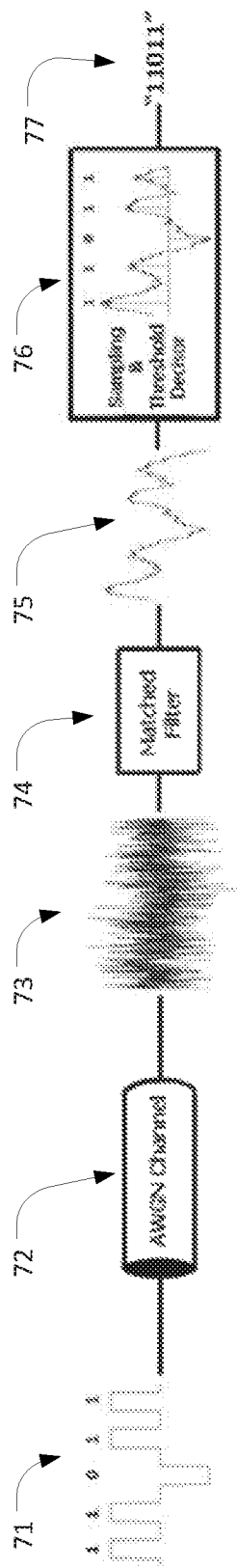
FIG. 7 is a block diagram of a process for using a matched filter to analyze a noisy signal.

With respect to multipath, the matched filter does two things. First, as "time zero" is known, the filter is automatically synchronized to any given path, and all the other paths are separated by at least the duration of a chip (i.e., the paths are resolvable), the filter will attenuate the other paths (i.e., it will reduce the interference caused by the other paths). Second, the matched filter will do the same thing for any resolvable path, resulting in the matched filter output being a sequence of time-displaced narrow pulses representing the times of arrival of the multiple arriving paths. As an example of how a matched filter would enable extraction of the desired brain remitted, electronically coded optical signal we refer to FIG. 7, which shows the use of a matched filter in extracting weak digital signals in the presence of additive white Gaussian noise (AWGN). The raw encoded electrical signal 71 traverses a noisy channel 72 that adds AWGN to the signal, resulting in the noisy, encoded signal 73. The noisy channel 72 is representative of the noise that exists when a noisy optical signal is detected by a PD. Thus, the noisy, encoded signal 73 is similar to the electrical signal output by the PDs of a cerebral oximeter in that it contains the coded signal. The AWGN of the noisy, encoded signal 73 makes it difficult to detect the underlying encoded signal. But passing the noisy, encoded signal 73 through a matched filter 74 removes much of the AWGN, resulting in a signal from which a digital signal can be extracted. Using sampling and threshold techniques 76 known in the art, the digital, encoded signal 77 can be extracted from the noisy, encoded signal 73.

Figure 8:
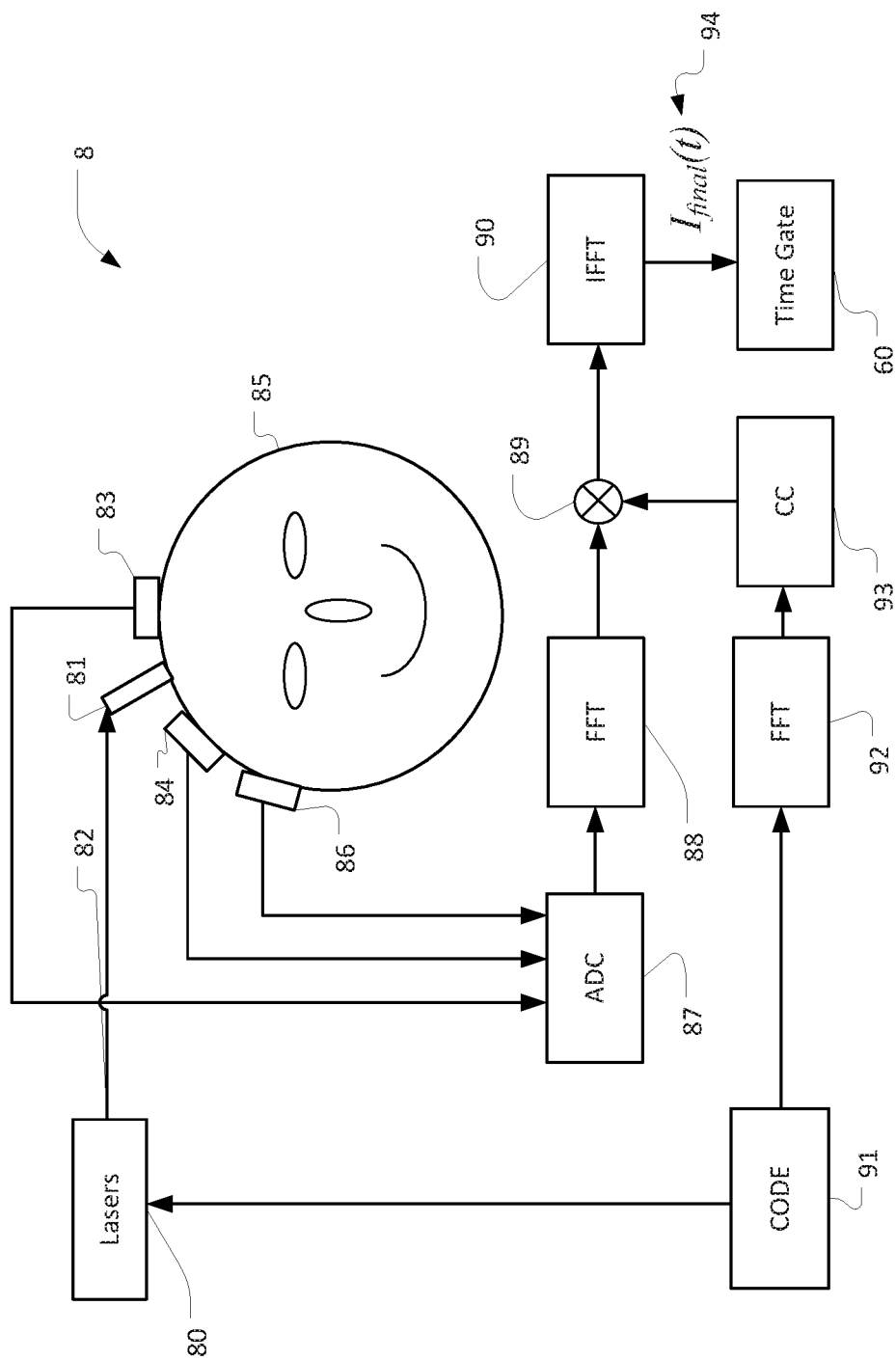
FIG. 8 is a block diagram of the electronic components of a cerebral oximeter using a matched filter configuration.

The matched filter 74 uses Fast Fourier Transform (FFT) processing which, in turn, uses buffering and caching of samples at the full input data rate. Assuming that an optical signal is received from a path that passes through the brain, and multiple other paths due to surface leakage, the matched filter does not completely eliminate the surface leakage, but it does resolve the different paths in time. Thus, if the path of interest is known, the output of the matched filter can be time-gated to eliminate the unwanted paths. This is illustrated in the schematic of FIG. 8 which shows the components used in a matched filter configuration of the device. In the matched filter configuration, computations are carried out in the frequency domain (as opposed to the time domain operations involved in the correlator), and generally involve FFT circuit components. Referring to FIG. 8, lasers 80 emit light that is coupled to the head 85 of a person via optical coupler 81. In this case, two lasers are used—a first laser emitting light with a wavelength less than 800 nm and a second laser emitting light with a wavelength greater than 800 nm. The lasers 80 are coupled to an optical coupler 81 via optical fiber 82. The optical coupler 81 may include one or more lenses for concentrating the light from the lasers 80 on a particular portion of the head 85. The light then propagates through the head 85 via multiple paths through the scalp, skull and brain. The lasers may be correlated such that the laser pulses emitted by each laser are emitted simultaneously, but encoded with two different optical PN codes, which are controlled by code generator 91, which controls the electrical driving signal that controls the lasers 80.

Light that is scattered, both by brain tissue, the scalp and skull, is sensed by one or more PDs. In the case of FIG. 8, three PDs are shown: a first PD 83, a second PD 84 and a third PD 86. By spreading the multiple PDs around the surface of the head 85 in a particular arrangement, the light detected by the PDs can be used for geometric determination of the brain volume being sensed.

The time-varying coded PD signals from the first PD 83, the second PD 84 and the third PD 86 are directed into an analog-to-digital converter (ADC) 87 to convert the analog signals from the PDs to digital detection signals. The digital detection signals are then mathematically analyzed using a FFT module. Similarly, the raw code information from the code generator 91 is analyzed using an FFT module 92. The FFT modules convert the digital signals on which they operate from the time-domain to the frequency domain. Thus, the output from FFT module 88 and FFT module 92 is a complex spectrum of the input signal. The complex spectrum output from FFT module 92 is conjugated using the complex conjugate module 93. Then, the conjugated spectrum is mixed with the detected spectrum from FFT module 88 at a mixer 89. The mixer 89 mixing the conjugated spectrum with the detected spectrum is an implementation of a matched filter. The resulting signal is then operated on by inverse FFT (IFFT) module 90, which converts an input frequency domain signal into the time domain, and outputs a final optical signal intensity 94 in the time domain (represented as $I_{final}(t)$).

The final optical signal intensity 94 is provided to a time gate 60 that is configured to filter the final optical signal intensity 94 based on a desired time of arrival. The time gate 60 may be implemented by a processor that selects a desired range of times that correspond to a region of interest within the head 85 of the subject. The time gating of the final optical signal intensity 94 allows the cerebral oximeter 8 to make measurements of the tissue at particular regions within the head 85 without interference from the other paths taken by the light from the light sources, such as light scattered through the scalp, light scattered by portions of the brain that are of no interest and background light from other sources.

Figure 9:
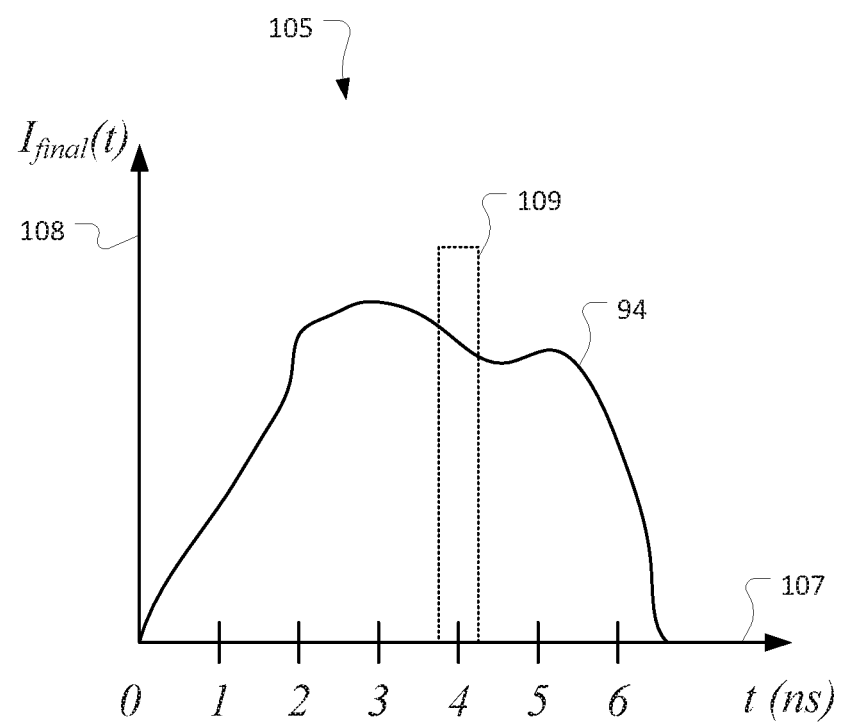
FIG. 9 is a graph if the intensity as a function of time resulting from performing cerebral oximetry.

Referring to FIG. 9, a graph 105 of the resulting optical signal intensity 94 in the time domain may be plotted as a function of time, where the time axis 107 represents the light path delay time and the y-axis 108 represents the intensity of the light at a particular time built up over multiple light pulses. The time gate 60 may be implemented after building up a time-of-arrival histogram. The user can, for example, select any light path delay time and refer to the corresponding light intensity signal value obtained from this graph. This gives the user the ability to determine the detected light intensity at any assumed light travel delay time, thus facilitating measurement of light remitted from any desired physical region of the brain without the confounding shorter light path delay time light signals due to light leakage across the surface or near-surface of the skull.

Time-of-arrival histograms and time gating may be performed for the two different light sources. Then, the light intensity for the signals associated with the two different lasers can then be compared at the same desired time-of-arrival to determine the oxygen saturation level at the location in the brain corresponding to the light path delay time for the desired time-of-arrival. For example, by selecting light path delay times known to be longer than the light surface leakage times of ~0.2 ns, the user can then eliminate the confounding light surface leakage artifacts. This, in turn, provides the user with the ability to select delay times corresponding to expected light remission times originating from brain tissue penetrations of various depths below the surface of the skull, typically expected to be >1 ns. In FIG. 9, a time gate 109 is illustrated as centered at a time-of-arrival of 4 ns with a gate width (e.g., duration) of 0.5 ns. Other gate widths may be used. For example, gate widths of less than 0.5 ns will filter the intensity more to a smaller region of the brain and gate widths of more than 0.5 ns will filter the intensity less, providing an intensity associated with a larger portion of the brain.

The aforementioned modules of FIG. 8 may be implemented using a field programmable gate array (FPGA) or an application specific integrated circuit (ASIC). Alternatively, the modules may be implemented using software executing on a processor.

Figure 10:
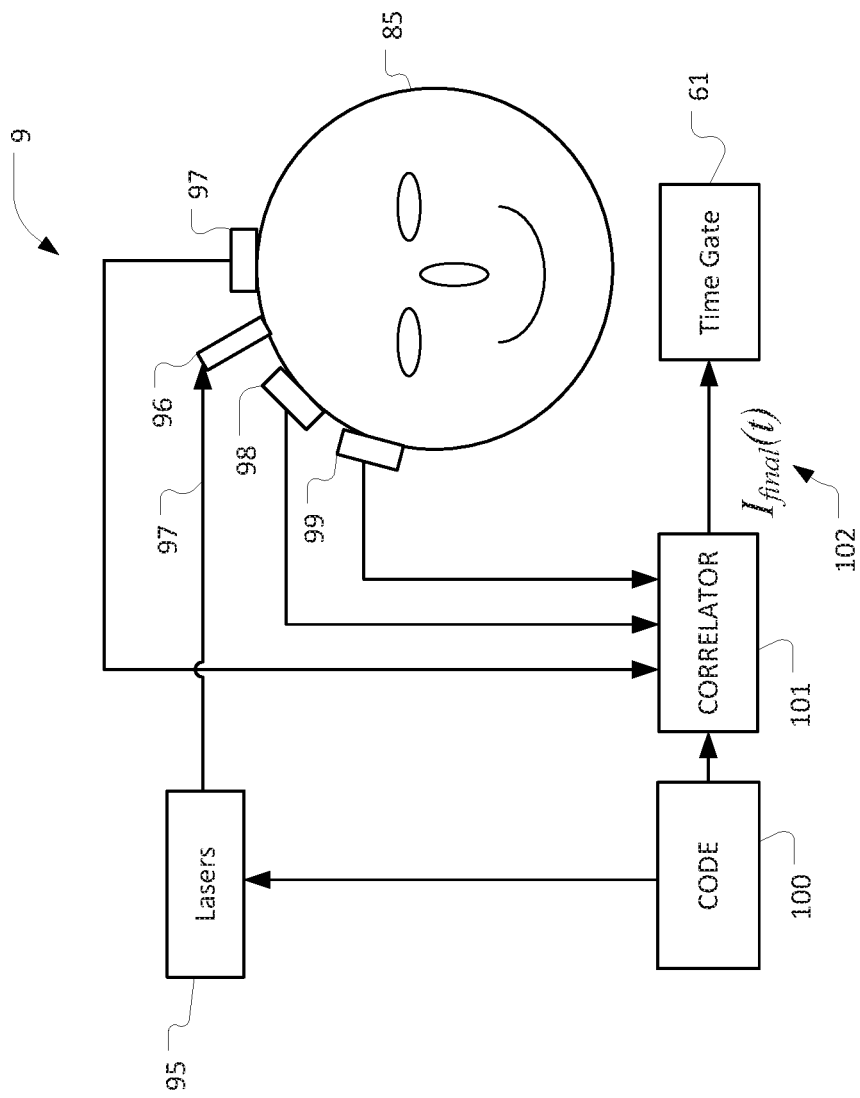
FIG. 10 is a block diagram of the electronic components of a cerebral oximeter using a correlator configuration.

Referring to FIG. 10, a cerebral oximeter 9 using a correlator configuration is shown in the schematic of FIG. 10. The cerebral oximeter 9 carries out all electronic operations in the time domain and does not convert signals to the frequency domain, as was done in the cerebral oximeter 8 using the matched filter configuration. As in the case of the cerebral oximeter 8 using the matched filter configuration, the light from the lasers 95 is transmitted from the lasers to an optical coupler 96. The light is modulated with a code received from the code generator 100. A first laser that emits light of a first wavelength is modulated with a first code and a second laser that emits light of a second wavelength is modulated with a second code. The light exits the optical coupler 96 and is incident on to the head 85 of a subject. Light from various paths through the head 85 are detected by a first PD 97, a second PD 98 and a third PD 99 (though any number of PDs may be used). The detected light includes surface leakage as well as brain tissue remitted light. The analog signals output by the PDs are fed into a correlator 101, which is programmed with the digital laser modulation code received from code generator 100 using firmware consisting of logic circuitry using, for example, the Reconfigurable Open Architecture Computing Hardware (ROACH) or similar firmware. The electrical signal 102 output from the correlator 101 is the detected light signal intensity as a function of light path time delay (represented as $I_{final}(t)$) and is provided to a time gate 61. The time gate 61 may be implemented by a processor that selects a desired range of times that correspond to a region of interest within the head 85 of the subject. The time gating of the electrical 102 allows the cerebral oximeter 8 to make measurements of the tissue at particular regions within the head 85 without interference from the other paths taken by the light from the light sources, such as light scattered through the scalp, light scattered by portions of the brain that are of no interest and background light from other sources.

The cerebral oximeter 9 can determine the detected light intensity for any assumed light travel delay time, thus facilitating measurement of light remitted from any desired physical region of the brain without the confounding shorter light path delay time light signals due to light leakage across the surface or near-surface of the skull. An advantage of the correlator configuration over that of the matched filter is that in the correlator the electronics are simpler and less expensive than in the matched filter. However, once designed, verified and proven effective, the cost for high volume manufactured instruments based on either the matched filter or the correlator could be significantly reduced.

Figure 11:
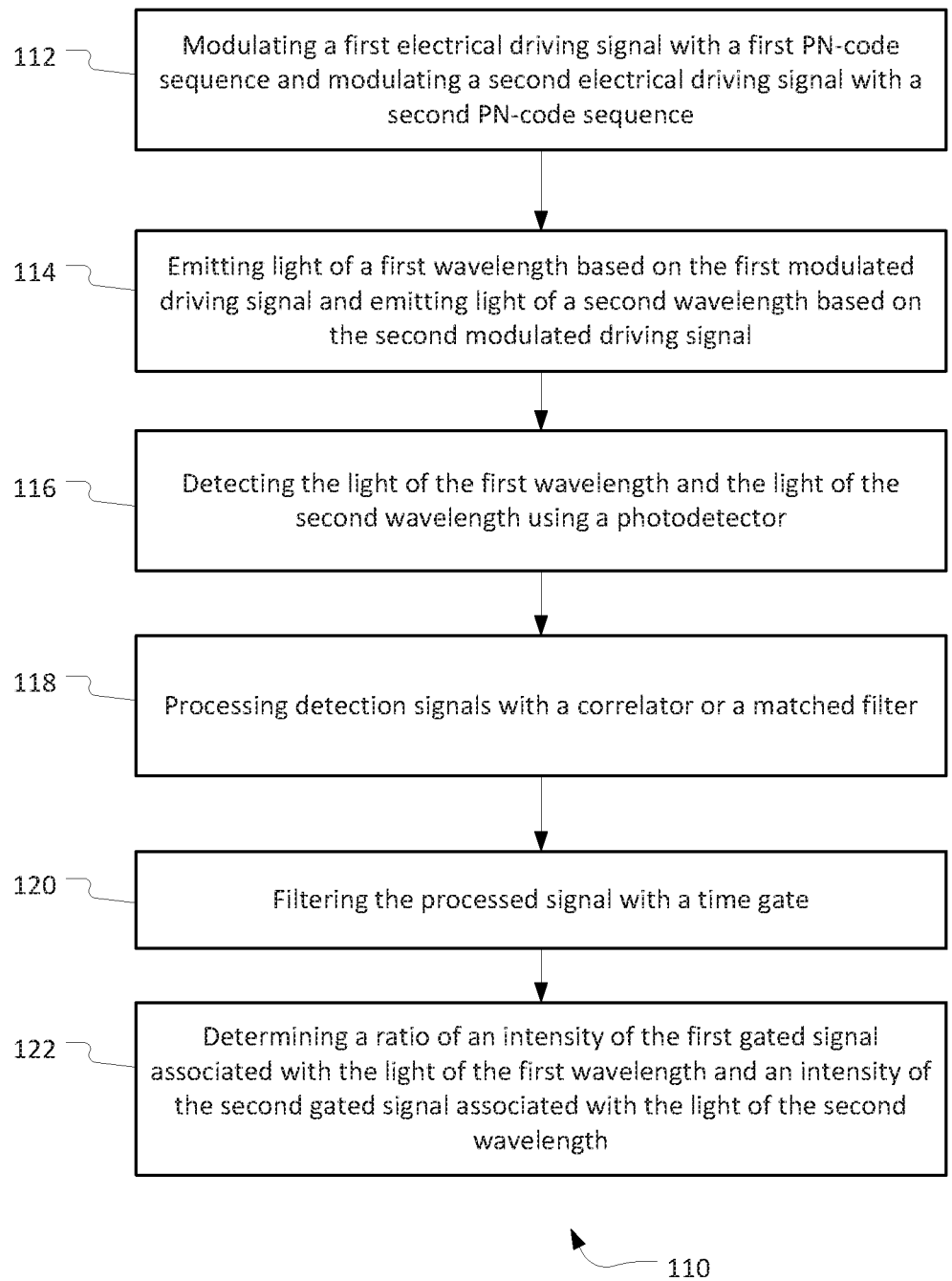
FIG. 11 is a flow diagram of a method of performing cerebral oximetry.

Referring to FIG. 11, a method 110 of performing oximetry includes the stages shown. The method 110 is, however, an example only and not limiting. The method 110 can be altered, e.g., by having stages added, removed, rearranged, combined, performed concurrently, and/or having single stages split into multiple stages.

At stage 112, the method 110 includes modulating a first electrical driving signal with a first PN-code sequence and modulating a second electrical driving signal with a second PN-code sequence. The first PN-code sequence is different from the second PN-code sequence such that the two codes can be distinguished from one another. In an example, the code generator 91 may be a means for modulating the first and second electrical driving signals.

At stage 114, the method 110 includes emitting light of a first wavelength based on the first modulated driving signal and emitting light of a second wavelength based on the second modulated driving signal. In an example, the lasers 80 may be a means for emitting light. A first laser uses the first electrical driving signal to generate and emit light of the first wavelength and second laser uses the second electrical driving signal to generate and emit light of the second wavelength. The first wavelength and the second wavelength are selected such that the absorption by both oxygen saturated and unsaturated hemoglobin is significantly different, as illustrated in FIG. 1. For example, the first wavelength may be less than 800 nm and the second wavelength may be greater than 800 nm.

At stage 116, the method 110 includes detecting the light of the first wavelength and the light of the second wavelength using a photodetector. One or more photo detectors 83, 84, 86 may be a means for detecting the light. More than one photodetector may be used to detect the light. For example, the light of the first wavelength may be detected by a first photodetector and the light of the second wavelength may be detected by a second photodetector. The photodetectors may use spectral filters to exclude other wavelengths of light. For example, the first photodetector may include a spectral filter that prevents the detection of light of the second wavelength. The first photodetector generates a first detection signal in response to the detection of the light of the first wavelength and the second photodetector generates a second detection signal in response to the detection of the light of the second wavelength.

At stage 118, the method 110 includes processing the detection signals with a correlator or a matched filter. As discussed above in connection with FIGS. 8-9, the first detection signal may be correlated with the first PN-code and the second detection signal may be correlated with the second PN-code using a correlator. Alternatively, the detection signals may be processed by an ADC and the first detection signal may be processed with a first matched filter and the second detection signal may be processed with a second matched filter. The result of either processing is a first processed signal and a second processed signal.

At stage 120, the method 110 includes filtering the processed signal with a time gate. Both the first processed signal and a second processed signal may be time gated to filter out a portion of the signals that corresponds to a region of interest. For example, if the portion of the brain being monitored for trauma is associated with a particular portion of the brain that corresponds to a first time and a first time duration, then the processed signals may be time gated such that only the portion of the signal corresponding to the first time duration around the first time is kept and the rest of the processed signal is ignored. The result of the time gating is a first gated signal associated with the light of the first wavelength and an intensity of the second gated signal associated with the light of the second wavelength.

At stage 122, the method 110 includes determining a ratio of an intensity of the first gated signal associated with the light of the first wavelength and an intensity of the second gated signal associated with the light of the second wavelength. The ratio of the intensity of the two signals is related to the oxygen saturation level of the hemoglobin in the patient's blood. By taking the ratio of the two intensities. The intensities used for the ratio may be a mean or median intensity or a peak intensity.

Figure 12:
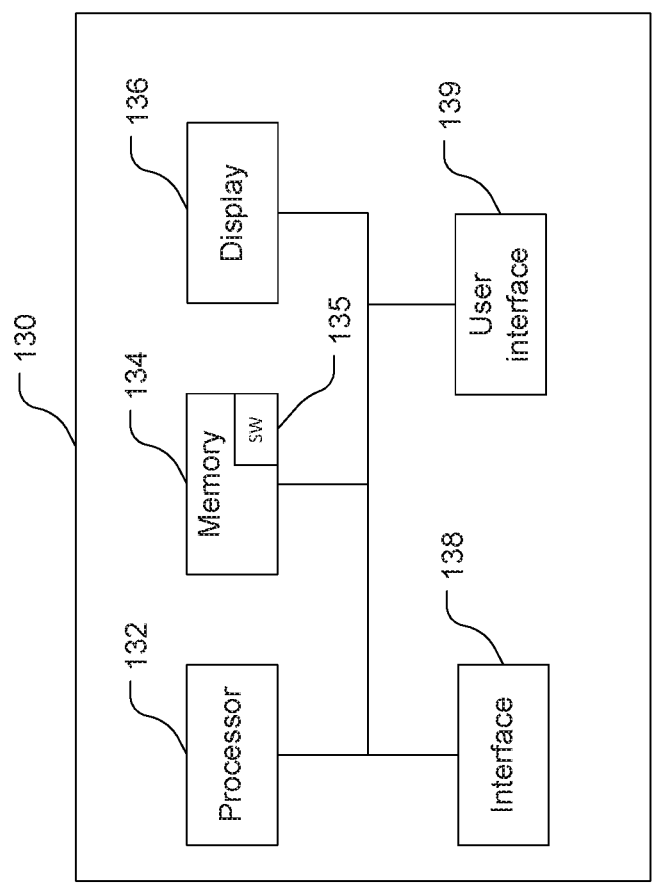
FIG. 12 is a computing system that may be used to implement cerebral oximetry.

Referring to FIG. 12, any of the above processing steps can be performed by a computing system 130. The computing system 130 includes a processor 132 and a memory 134 including software (SW) 135. The processor 132 is preferably an intelligent hardware device, for example a central processing unit (CPU) such as those made or designed by ARM®, Intel® Corporation, or AMD®, a microcontroller, an application specific integrated circuit (ASIC), a field programmable gate array (FPGA) etc. The processor 132 may include multiple separate physical entities that can be distributed in the computing system 130. The memory 134 may include random access memory (RAM) and/or read-only memory (ROM). The memory 134 is a non-transitory, processor-readable storage medium that stores the software 135 which is processor-readable, processor-executable software code containing instructions that are configured to, when performed, cause the processor 132 to perform various functions described herein. The description may refer only to the processor 132 performing the functions, but this includes other implementations such as where the processor 132 executes software and/or firmware. The software 135 may not be directly executable by the processor 132 and instead may be configured to, for example when compiled and executed, cause the processor 132 to perform the functions. Whether needing compiling or not, the software 135 contains the instructions to cause the processor 132 to perform the functions. The processor 132 is communicatively coupled to the memory 134. The processor 132 in combination with the memory 134 provide means for performing functions as described herein, for example, processing the signals generated by the photodetectors. The software 135 can be loaded onto the memory 134 by being downloaded via a network connection, uploaded from a disk, etc.

The computing system 130 includes an interface 138 for receiving the electrical signals from the photodetectors. Additionally, the computing system 130 includes a display 136 for displaying measurement results to a user of the computing system 130. The computing system 130 also includes a user interface 139 for receiving input from a user. The user interface 139 may include a keyboard, a mouse, a touchpad or a touchscreen interface. The user interface is configured to receive desired time-of-arrival information from a user of the computing system 130. For example, the user may provide a desired time-of-arrival and gate width for the time gate of the cerebral oximeter by entering values via the keyboard or selecting values with the mouse. Alternatively, the user may view the time-of-arrival spectrum on the display 136 and select a time-region of interest using the mouse.

OTHER CONSIDERATIONS

Other examples and implementations are within the scope and spirit of the disclosure and appended claims. For example, due to the nature of software and computers, functions described above can be implemented using software executed by a processor, hardware, firmware, hardwiring, or a combination of any of these. Features implementing functions may also be physically located at various positions, including being distributed such that portions of functions are implemented at different physical locations.

As used herein, "or" as used in a list of items prefaced by "at least one of" or prefaced by "one or more of" indicates a disjunctive list such that, for example, a list of "at least one of A, B, or C," or a list of "one or more of A, B, or C" means A or B or C or AB or AC or BC or ABC (i.e., A and B and C), or combinations with more than one feature (e.g., AA, AAB, ABBC, etc.).

As used herein, unless otherwise stated, a statement that a function or operation is "based on" an item or condition means that the function or operation is based on the stated item or condition and may be based on one or more items and/or conditions in addition to the stated item or condition.

Further, an indication that information is sent or transmitted, or a statement of sending or transmitting information, "to" an entity does not require completion of the communication. Such indications or statements include situations where the information is conveyed from a sending entity but does not reach an intended recipient of the information. The intended recipient, even if not actually receiving the information, may still be referred to as a receiving entity, e.g., a receiving execution environment. Further, an entity that is configured to send or transmit information "to" an intended recipient is not required to be configured to complete the delivery of the information to the intended recipient. For example, the entity may provide the information, with an indication of the intended recipient, to another entity that is capable of forwarding the information along with an indication of the intended recipient.

Other examples and implementations are within the scope and spirit of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations.

Further, more than one invention may be disclosed.

Substantial variations to described configurations may be made in accordance with specific requirements. For example, customized hardware might also be used, and/or particular elements might be implemented in hardware, software (including portable software, such as applets, etc.), or both. Further, connection to other computing devices such as network input/output devices may be employed.

Common forms of physical and/or tangible computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, EPROM, a FLASH-EPROM, any other memory chip or cartridge, a carrier wave as described hereinafter, or any other medium from which a computer can read instructions and/or code.

The methods, systems, and devices discussed above are examples. Various configurations may omit, substitute, or add various procedures or components as appropriate. For instance, in alternative configurations, the methods may be performed in an order different from that described, and that various steps may be added, omitted, or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations provides a description for implementing described techniques. Various changes may be made in the function and arrangement of elements without departing from the spirit or scope of the disclosure.

Also, configurations may be described as a process which is depicted as a flow diagram or block diagram. Although each may describe the operations as a sequential process, many of the operations can be performed in parallel or concurrently. In addition, the order of the operations may be rearranged. A process may have additional stages or functions not included in the figure. Furthermore, examples of the methods may be implemented by hardware, software, firmware, middleware, microcode, hardware description languages, or any combination thereof. When implemented in software, firmware, middleware, or microcode, the program code or code segments to perform the tasks may be stored in a non-transitory computer-readable medium such as a storage medium. Processors may perform the described tasks.

Components, functional or otherwise, shown in the figures and/or discussed herein as being connected or communicating with each other are communicatively coupled. That is, they may be directly or indirectly connected to enable communication between them.

Having described several example configurations, various modifications, alternative constructions, and equivalents may be used without departing from the spirit of the disclosure. For example, the above elements may be components of a larger system, wherein other rules may take precedence over or otherwise modify the application of the invention. Also, a number of operations may be undertaken before, during, or after the above elements are considered. Accordingly, the above description does not bound the scope of the claims.

A statement that a value exceeds (or is more than) a first threshold value is equivalent to a statement that the value meets or exceeds a second threshold value that is slightly greater than the first threshold value, e.g., the second threshold value being one value higher than the first threshold value in the resolution of a computing system. A statement that a value is less than (or is within) a first threshold value is equivalent to a statement that the value is less than or equal to a second threshold value that is slightly lower than the first threshold value, e.g., the second threshold value being one value lower than the first threshold value in the resolution of a computing system.

What is claimed is:

1. A cerebral oximeter comprising:
   a first light source configured to emit light within a first range of wavelengths in response to a first electrical signal;
   a second light source configured to emit light within a second range of wavelengths in response to a second electrical signal;
   a first photodetector configured to detect at least a portion of the light emitted from the first light source;
   a second photodetector configured to detect at least a portion of the light emitted from the second light source;
   a pseudonoise (PN) code modulator configured to modulate the first electrical signal and the second electrical signal using a spreading sequence to occupy an electrical bandwidth greater than necessary to send optical signal pulse amplitude information to a photodetector;
   a correlator or a matched filter operably coupled to an output of the first photodetector and an output of the second photodetector and configured to output detected light signal intensity as a function of light path time delay; and
   a time gate operably coupled to an output of the correlator or the matched filter and configured to filter a first detected signal intensity from the first photodetector and a second detected signal intensity from the second photodetector based on a desired time-of-arrival.

2. The cerebral oximeter of claim 1, wherein the first photodetector and the second photodetector have an electrical bandwidth sufficient to detect the pseudonoise (PN) code modulated spread spectrum light signals.

3. The cerebral oximeter of claim 1, wherein the first photodetector and the second photodetector are configured to receive light signals from the first light source and the second light source in addition to thermal noise and external interference.

4. The cerebral oximeter of claim 1, further comprising:
   detection circuitry with sufficient electrical bandwidth so that an autocorrelation function of the spreading sequence has a main lobe that is narrower than a time separation of a desired signal and at least one multipath signal.

5. The cerebral oximeter of claim 1, further comprising a processor configured to:
   measure characteristics of an optical channel traversed by the light emitted by the first light source or the light emitted by the second light source; and
   enhance an accuracy of a mathematical model used to model propagation of light from the first light source to the first photodetector.

6. The cerebral oximeter of claim 1, wherein the matched filter is a passive filter.

7. The cerebral oximeter of claim 6, wherein the passive filter is matched to the spreading sequence.

8. The cerebral oximeter of claim 7, wherein the only input to the passive filter is received from the first photodetector or the second photodetector.

9. The cerebral oximeter of claim 7, further comprising a processor configured to generate a time-of-arrival spectrum, which grows more precise with increasing number of detected laser pulses.

10. A method of performing cerebral oximetry comprising:
   emitting light within a first range of wavelengths in response to a first electrical signal; emitting light within a second range of wavelengths in response to a second electrical signal;
   detecting at least a portion of the light emitted from a first light source; detecting at least a portion of the light emitted from a second light source;
   modulating the first electrical signal and the second electrical signal using a spreading sequence to occupy an electrical bandwidth greater than necessary to send optical signal pulse amplitude information to a photodetector;
   processing a first detection signal from a first photodetector and a second detection signal from a second photodetector with a correlator or a matched filter, wherein each of the processed first and second detection signals indicative of a function of light path time delay; and
   filtering the processed first and second detection signals with a time gate based on a desired time of arrival.

11. The method of claim 10, wherein the electrical bandwidth is sufficient to send a pseudonoise (PN) code modulated spread spectrum light signal.

12. The method of claim 10, wherein the first photodetector and the second photodetector are configured to receive light signals from the first light source and the second light source in addition to thermal noise and external interference.

13. The method of claim 10, further comprising determining an autocorrelation function of the spreading sequence including a main lobe that is narrower than a time separation of a desired signal and at least one multipath signal.

14. The method of claim 10, further comprising:
   measuring characteristics of an optical channel traversed by the light emitted from the first light source or the light emitted from the second light source; and
   enhancing an accuracy of a mathematical model used to model propagation of light from the first light source to the first photodetector based at least in part on the measured characteristics of the optical channel.

15. The method of claim 10, wherein processing the first detection signal and the second detection signal includes receiving an output from the matched filter, wherein the matched filter is a passive filter.

16. The method of claim 15, wherein the passive filter is matched to the spreading sequence.

17. The method of claim 16, wherein the only input to the passive filter is received from the first photodetector or the second photodetector.

18. The method of claim 10, further comprising generating a time-of-arrival spectrum based on detecting the light emitted from the first light source and the second light source.

19. A cerebral oximeter comprising:
   first emitting means for emitting light within a first range of wavelengths in response to a first electrical signal;
   second emitting means for emitting light within a second range of wavelengths in response to a second electrical signal;
   a detecting means for detecting at least a portion of the light emitted from the first emitting means and for detecting at least a portion of the light emitted from the second emitting means;
   modulating means for modulating the first electrical signal and the second electrical signal using a spreading sequence to occupy an electrical bandwidth greater than necessary to send optical signal pulse amplitude information to the detecting means;
   a correlating means for determining a detection light signal intensity of a function of a light path time delay based on detected light from the detecting means; and
   filtering means configured to filter a first detection light signal intensity from the correlating means and a second detection light signal intensity from the correlating means based on a desired time-of-arrival.

20. The cerebral oximeter of claim 19 wherein the detecting means includes a first photodetector and a second photodetector.

* * * * *